(12) United States Patent
Liu et al.

(10) Patent No.: US 12,161,338 B2
(45) Date of Patent: Dec. 10, 2024

(54) SUTURE-FREE CLASP FOR VASCULAR ANASTOMOSIS

(71) Applicant: BEIJING PERCUTEK THERAPEUTICS CO., LTD., Beijing (CN)

(72) Inventors: Ying Liu, Beijing (CN); Fei Li, Beijing (CN); Yonghe Dong, Beijing (CN); Qingqing Du, Beijing (CN); Wuen Han, Beijing (CN); Fan Yang, Beijing (CN)

(73) Assignee: BEIJING PERCUTEK THERAPEUTICS CO., LTD., Beijing (CN)

( * ) Notice: Subject to any disclaimer, the term of this patent is extended or adjusted under 35 U.S.C. 154(b) by 686 days.

(21) Appl. No.: 17/422,771

(22) PCT Filed: Jan. 21, 2020

(86) PCT No.: PCT/CN2020/073596
§ 371 (c)(1),
(2) Date: Jul. 14, 2021

(87) PCT Pub. No.: WO2021/036199
PCT Pub. Date: Mar. 4, 2021

(65) Prior Publication Data
US 2022/0061846 A1    Mar. 3, 2022

(30) Foreign Application Priority Data
Aug. 29, 2019  (CN) .......................... 201910811226.2

(51) Int. Cl.
*A61B 17/11*    (2006.01)
*A61B 17/122*   (2006.01)

(52) U.S. Cl.
CPC ............ *A61B 17/11* (2013.01); *A61B 17/122* (2013.01); *A61B 2017/1107* (2013.01); *A61B 2017/1132* (2013.01)

(58) Field of Classification Search
CPC ................. A61B 2017/1107; A61B 2017/1132
See application file for complete search history.

(56) References Cited

U.S. PATENT DOCUMENTS 4,667,662 A * 5/1987 Titone .................... A61B 17/82
                                                      606/74
5,314,437 A * 5/1994 Holtsch ............. A61B 17/1327
                                                      606/151

(Continued)

FOREIGN PATENT DOCUMENTS

CN       202173424 U     3/2012
CN       205831862 U    12/2016

(Continued)

*Primary Examiner* — Elizabeth Houston
*Assistant Examiner* — Jonathan A Hollm
(74) *Attorney, Agent, or Firm* — S.J. Intellectual Property LTD.

(57) ABSTRACT

A suture-free clasp for vascular anastomosis, which relates to the technical field of vascular anastomosis. The clasp comprises a first end part (1), a second end part (2), a rotating shaft (3), a binding belt (4) and a rotation-stopping structure (5). The rotating shaft (3) is rotationally installed on the first end part (1); and one end of the binding belt (4) is fixed to the rotating shaft (3), and the other end of the binding belt (4) is fixed to the second end part (2). The second end part (2) is configured to be able to buckle with the first end part (1); and the rotation-stopping structure (5) is arranged between the first end part (1) and the rotating shaft (3), and the rotation-stopping structure (5) is configured to be able to lock the rotating shaft (3) on the first end part (1). The suture-free clasp for vascular anastomosis reduces the influences of human factors of doctor during (Continued)

vascular anastomosis on the knotting position and knotting strength, thereby solving the technical problems in the prior art in which knotting operations are difficult, pseudoaneurysms occur since slipping happens easily during knotting which then causes blood leakage, and readjustments are difficult after knotting is complete.

18 Claims, 4 Drawing Sheets

(56) References Cited

U.S. PATENT DOCUMENTS

| | | |
|---|---|---|
| 5,752,966 A | 5/1998 | Chang |
| 7,585,306 B2 | 9/2009 | Abbott et al. |
| 2006/0004394 A1 | 1/2006 | Amarant |
| 2008/0215134 A1* | 9/2008 | Lawrence-Brown ... A61L 31/18 623/1.34 |
| 2010/0049241 A1* | 2/2010 | Persson .............. A61B 17/1322 606/203 |
| 2019/0247054 A1 | 8/2019 | Fostad Moe |

FOREIGN PATENT DOCUMENTS

| | | | |
|---|---|---|---|
| CN | 106726001 A | 5/2017 | |
| CN | 107280724 A * | 10/2017 | ............ A61B 17/11 |
| CN | 208259728 U | 12/2018 | |
| CN | 110477985 A | 11/2019 | |
| JP | H64500246 A | 2/1989 | |
| WO | WO2004028378 A1 | 4/2004 | |

\* cited by examiner

SUTURE-FREE CLASP FOR VASCULAR ANASTOMOSIS

CROSS-REFERENCE TO RELATED APPLICATION

The present disclosure claims the priority to the Chinese patent application filed with the Chinese Patent Office on Aug. 29, 2019 with the filing number 201910811226.2, and entitled "Suture-free Clasp for Vascular Anastomosis", the contents of which are incorporated herein by reference in entirety.

TECHNICAL FIELD

The present disclosure relates to the technical field of vascular anastomosis, in particular, to a suture-free clasp (i.e., fastening ring) for vascular anastomosis.

BACKGROUND ART

In the medical field, aortic diseases such as aortic aneurysm, particularly aortic dissection aneurysm, have the characteristics of acute onset, rapid disease progression, complex disease condition, and extremely high mortality. Most patients with aortic aneurysm including aortic dissection aneurysm need surgical treatment, and an artificial large blood vessel is used to replace a diseased artery during treatment. Due to severe edema and high brittleness of aortic tissues in most lesions, surgical operation of anastomosis of the artificial large blood vessel and the patient's diseased aorta is extremely complex, the technical difficulty is high, the anastomotic stoma is easy to bleed, and the anastomotic time is long, so that the time of Deep Hypothermia Circulatory Arrest (DHCA) is prolonged, and serious complications such as ischemic brain injury or spinal cord injury are extremely easy to occur. In order to reduce the aortic anastomosis time and reduce the probability of anastomotic stoma bleeding, so as to reduce related complications and improve the surgical treatment success rate of the aortic aneurysm patients, cardiovascular surgeons start to perform aortic anastomosis using a sutureless method. This sutureless method is a sutureless intraluminal graft (SIG for short), in which positions of the patient's autologous blood vessel that needs to be anastomosed with two ends of the artificial blood vessel are two broken ends of the patient's autologous blood vessel, the artificial blood vessel with either end provided with a fixing ring is placed inside the two broken ends of the patient's autologous blood vessel, respectively, and then tied at parts corresponding to the fixing rings outside the autologous blood vessel by a tying belt, so as to complete the fixation and anastomosis.

Conventionally, in SIG surgery, a vascular anastomosis process is usually completed by a doctor using an umbilical cord on site to knot and fix, while this process has the disadvantage of uncontrollable force of knotting and fixing: when the silk thread is too thin and the force is too large, it is easy to generate a cutting effect on the patient's autologous blood vessel; and if the force is too small, it may cause slippage and blood leakage to form pseudoaneurysm.

Currently, as an improvement on the above technique, doctors start to knot and fix with a silk belt having a certain width. However, a plurality of turns are required, whether using the silk thread or the silk belt, the doctor's visual field and operation direction should be perpendicular to an axis of the patient's autologous blood vessel so that the winding distance of the silk thread or silk belt is the shortest, thus, the shedding time of the silk thread or silk belt is prolonged as much as possible. However, the aorta has an aortic arch inclined backward after exiting from the heart, which makes the visual field and operating space of the doctor for aorta operation quite limited, therefore, it is quite difficult to obtain the most advantageous position for knotting during the operation, particularly when ligation of broken end of the aortic arch is involved. In addition, once the knotting is completed, the silk belt will be tightly attached to the patient's autologous blood vessel, which makes it quite difficult for the doctor to disengage or readjust.

That is to say, although the doctors knot in the SIG surgery with the silk belt instead of the silk thread to perform vascular anastomosis, and achieve the effect of avoiding the cutting effect, at present, there are still the technical problems that the knotting position and strength are artificially affected by the operator to a large extent, causing difficult knotting operation, easy slippage of the knot to cause blood leakage to thereby form pseudoaneurysm, and difficult readjustment after the knotting is completed.

SUMMARY

Objectives of the present disclosure include, for example, providing a suture-free clasp for vascular anastomosis, so as to reduce the influence of human factors of doctors on the knotting position and knotting strength during vascular anastomosis, further solve the technical problems of difficult knotting operation, easy slippage of the knot to cause blood leakage and thereby form pseudoaneurysm, and difficult readjustment after the knotting is completed, existing in the prior art.

An embodiment of the present disclosure provides a suture-free clasp for vascular anastomosis, including a first end part, a second end part, a rotating shaft, a binding belt, and a rotation-stopping structure, wherein the rotating shaft is rotationally installed on the first end part; one end of the binding belt is fixed on the rotating shaft, the other end of the binding belt is fixed on the second end part; the second end part is configured to be capable of being snap-fitted with the first end part; and the rotation-stopping structure is provided between the first end part and the rotating shaft, and the rotation-stopping structure is configured to be capable of locking the rotating shaft to the first end part.

In an optional embodiment, the rotation-stopping structure comprises a ratchet and a pawl, wherein the ratchet is provided on a circumferential surface of the rotating shaft; one end of the pawl is connected to the first end part, and the pawl is configured to always have a moving tendency to slide towards a position between roots of two adjacent teeth of the ratchet.

In an optional embodiment, one end of the pawl is connected to the first end part in a detachable manner.

In an optional embodiment, the first end part comprises a first end part body and a limiting portion provided on the first end part body.

In an optional embodiment, the limiting portion and the first end part body are integrally formed, as an integral structure.

In an optional embodiment, the limiting portion is a structure fixed on the first end part body.

In an optional embodiment, the limiting portion has an accommodating groove, a fitting hole is provided on the first end part body in a position corresponding to the accommodating groove of the limiting portion.

In an optional embodiment, a fitting portion is connected to one end of the pawl, and the fitting portion is fitted into the fitting hole of the first end part body, and an end portion of an end of the pawl connected to the fitting portion is clamped in the accommodating groove of the limiting portion.

In an optional embodiment, the pawl is made of an elastic material.

In an optional embodiment, the elastic material is a metal material or a polymer material.

In an optional embodiment, the rotation-stopping structure comprises a ratchet and an end protective cover,
  wherein the ratchet is provided on a circumferential surface of the rotating shaft;
  the first end part is provided with fixing holes in positions between adjacent teeth of the ratchet; the end protective cover comprises a cover body and pins connected to the cover body; and
  the fixing holes and the pins are respectively at least two; and the at least two pins are correspondingly inserted into the fixing holes.

In an optional embodiment, the fixing holes and the pins are respectively four or more.

In an optional embodiment, a long hole is provided in the middle of the rotating shaft, and the binding belt is fixed on the rotating shaft in a manner that one end of the binding belt is threaded through the long hole and then is stitched with a remaining part of the binding belt.

In an optional embodiment, a long hole is provided in the middle of the rotating shaft, and the binding belt is fixed on the rotating shaft in a manner that one end of the binding belt is threaded through the long hole and then is joined with a remaining part of the binding belt.

In an optional embodiment, the binding belt is fixed on the rotating shaft in a manner that one end of the binding belt is threaded through the long hole and then is glued, welded, heat-sealed or stitched with a remaining part of the binding belt.

In an optional embodiment, the second end part comprises a rod portion and end flanges respectively provided at both ends of the rod portion;
  the first end part is provided with a snap-fit groove and arc-shaped fixing portions; the snap-fit groove is configured to be capable of accommodating the rod portion; and the arc-shaped fixing portion is formed at either end of the snap-fit groove in a length direction, and is configured to be capable of being clamped with the end flange.

In an optional embodiment, the first end part is provided with a rotating shaft mounting groove, a mounting hole is provided on an end surface of either end of the rotating shaft mounting groove, one end of the rotating shaft is inserted into one of the mounting holes, and the other end of the rotating shaft is inserted into the other mounting hole.

In an optional embodiment, the rotating shaft is made of a polymer injection molding material.

In an optional embodiment, a side of the first end part attached to an artificial blood vessel is of an arc shape.

In an optional embodiment, a marker is provided on at least one of a middle portion of the binding belt, the rotating shaft, and the second end part.

In an optional embodiment, the marker is made of a metal.

In an optional embodiment, an operating portion is provided at an end portion of the rotating shaft, and the operating portion is configured to be capable of cooperating with a surgical instrument so as to enable the rotating shaft to rotate.

In an optional embodiment, the operating portion is a polygonal operation hole provided in the end portion of the rotating shaft.

In an optional embodiment, the operating portion is a polygonal protrusion provided on the end portion of the rotating shaft.

In an optional embodiment, scales are set on an outer peripheral surface of the binding belt.

In an optional embodiment, the binding belt is made of a flexible material.

The suture-free clasp for vascular anastomosis provided in the embodiments of the present disclosure can achieve the following beneficial effects:
  the embodiments of the present disclosure provide a suture-free clasp for vascular anastomosis, including a first end part, a second end part, a rotating shaft, a binding belt, and a rotation-stopping structure; the rotating shaft is rotationally installed on the first end part; one end of the binding belt is fixed on the rotating shaft, the other end of the binding belt is fixed on the second end part; the second end part is configured to be capable of being snap-fitted with the first end part; and the rotation-stopping structure is provided between the first end part and the rotating shaft, and the rotation-stopping structure is configured to be capable of locking the rotating shaft to the first end part.

In use, end portions of the artificial blood vessel are disposed between broken ends of the patient's autologous blood vessel and the fixing rings, then the suture-free clasp for vascular anastomosis is snap-fitted outside the broken ends of the patient's autologous blood vessel, wherein a snap-fitting process is as follows:
  first, the second end part and the first end part are snap-fitted to each other; then, the rotating shaft is rotated, so that the binding belt is tightened until the broken ends of the patient's autologous blood vessel are attached to the artificial blood vessel, and the rotation-stopping structure locks the rotating shaft to the first end part, thus completing a tightening and fixing process; when readjustment is needed, the suture-free clasp for vascular anastomosis may be loosened just by releasing the rotation-stopping structure, for readjusting the tightness.

In the embodiments of the present disclosure, the vascular anastomosis operation is performed in a manner of rotating the rotating shaft after snap-fitting the second end part and the first end part to each other so as to tighten the binding belt, in place of a manner of completely relying on the doctor to manually wind a silk thread or a silk belt, followed by binding in the prior art. In an operation process, as it is not required that the doctor's visual field and operation direction must be perpendicular to an axis of the blood vessel, the influence of the doctor's human factors on the knotting position in the vascular anastomosis is reduced; meanwhile, the binding belt has a certain width and a certain frictional force, a larger pressure is applied on a larger area, which can avoid the cutting effect brought by the silk thread, and prevent local necrosis of the blood vessel. By controlling the depth and size of the operation hole of the rotating shaft, the final tightening strength of the binding belt of the doctor may be maintained within a range of stable force, further avoiding slippage and bleeding caused by a too low knotting force, and blood vessel necrosis caused by a too large force; the rotation-stopping structure may make the operation in the surgery more convenient, and long-term implantation safer. The binding belt is provided with scales and a developing ring, then the size and position of the binding belt may be observed in and after the operation, aiding to judge whether displacement exists. Compared with the prior art, the operations are simpler and more convenient, and when the locking state of the suture-free clasp needs to be readjusted, the clasp may be loosened just by releasing the rotation-stopping structure, so as to readjust the tightness and snap-fit position thereof, or release the snap-fit between the second end part and the first end part when the binding belt is in a loose state.

To sum up, the embodiments of the present disclosure at least reduce the influence of the doctor's human factors on the knotting position and knotting strength in the vascular anastomosis, and further solve the technical problems of difficult knotting operation, unstable knotting effect, and difficult readjustment after the knotting is completed, existing in the prior art, thus achieving convenient operation and controllable strength, facilitating adjustment and observation in and after the operation, then risks such as post-operation blood vessel necrosis and clasp slippage may be effectively reduced.

BRIEF DESCRIPTION OF DRAWINGS

In order to more clearly illustrate the technical solutions in specific embodiments of the present disclosure or in the prior art, accompanying drawings which need to be used for description of the specific embodiments or the prior art will be introduced briefly below, and apparently, the accompanying drawings in the description below merely show some embodiments of the present disclosure, and a person ordinarily skilled in the art still could obtain other drawings in light of these drawings without using creative efforts.

Reference signs: 1—first end part; 11—fixing hole; 12—snap-fit groove; 13—arc-shaped fixing portion; 14—rotating shaft mounting groove; 141—mounting hole; 2—second end part; 21—rod portion; 22—end flange; 3—rotating shaft; 31—long hole; 32—operating portion; 4—binding belt; 5—rotation-stopping structure; 51—ratchet; 52—pawl; 53—end protective cover; 531—cover body; 532—pin; 6—marker; 7—limiting portion.

DETAILED DESCRIPTION OF EMBODIMENTS

In order to make objectives, technical solutions, and advantages of the embodiments of the present disclosure clearer, the technical solutions in the embodiments of the present disclosure will be described clearly and completely below in conjunction with the accompanying drawings in the embodiments of the present disclosure, and apparently, some but not all embodiments of the present disclosure are described. Generally, components in the embodiments of the present disclosure described and shown in the accompanying drawings herein may be arranged and designed in different configurations.

Therefore, the detailed description below of the embodiments of the present disclosure provided in the accompanying drawings is not intended to limit the scope of the present disclosure to be protected, but merely represents chosen embodiments of the present disclosure. Based on the embodiments of the present disclosure, all of other embodiments obtained by those ordinarily skilled in the art without using creative efforts shall fall within the scope of protection of the present disclosure.

It should be noted that similar reference signs and letters represent similar items in the following accompanying drawings, therefore, once a certain item is defined in one accompanying drawing, it is not needed to be further defined or explained in subsequent accompanying drawings.

In the description of the present disclosure, it should be noted that orientation or positional relationships indicated by terms such as "center", "inner", and "outer", are based on orientation or positional relationships as shown in the drawings, or orientation or positional relationships of a product of the present disclosure when being conventionally placed in use, merely for facilitating describing the present disclosure and simplifying the description, rather than indicating or suggesting that related devices or elements have to be in the specific orientation or configured and operated in a specific orientation, therefore, they should not be construed as limitation to the present disclosure. Besides, terms such as "first" and "second" are merely used for distinctive description, but should not be construed as indicating or implying importance in the relativity.

In the description of the present disclosure, it should be further illustrated that, unless otherwise specifically regulated and defined, the terms "set", "install", and "connect" should be understood in a broad sense, for example, connection may be fixed connection, detachable connection, or integrated connection; it may be mechanical connection or electrical connection; it may be direct joining or indirect joining through an intermediary, and it also may be inner communication between two elements. For a person ordinarily skilled in the art, specific meanings of the above-mentioned terms in the present disclosure could be understood according to specific circumstances.

Some embodiments of the present disclosure are described in detail below in combination with the drawings. The following embodiments and the features in the embodiments may be combined with each other if there is no conflict.

Figure 1:
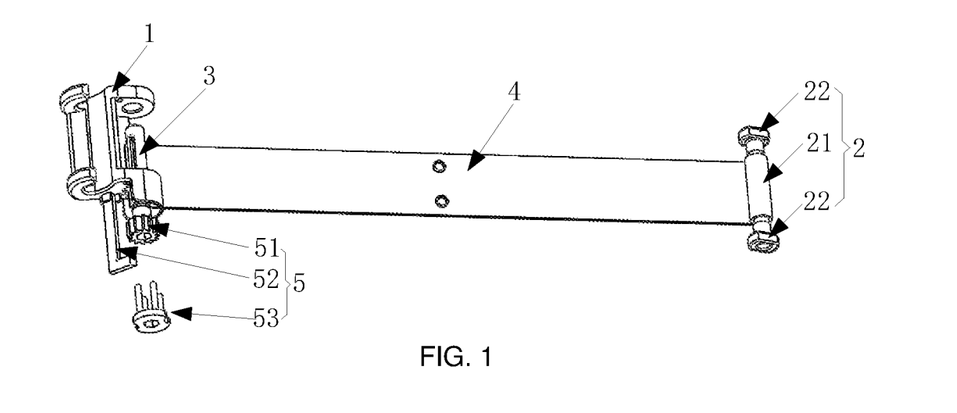
FIG. 1 is an exploded view of a whole structure of a suture-free clasp for vascular anastomosis provided in an embodiment of the present disclosure.
Figure 2:
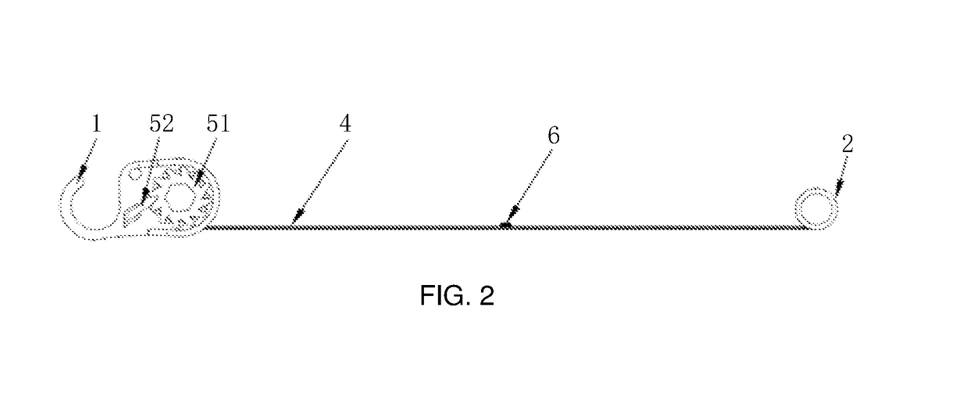
FIG. 2 is a front view of the whole structure of the suture-free clasp for vascular anastomosis provided in an embodiment of the present disclosure, without an end protective cover.

The present embodiment provides a suture-free clasp for vascular anastomosis. Referring to FIG. 1 and FIG. 2, the suture-free clasp for vascular anastomosis includes a first end part 1, a second end part 2, a rotating shaft 3, a binding belt 4, and a rotation-stopping structure 5; the rotating shaft 3 is rotationally installed on the first end part 1; one end of the binding belt 4 is fixed on the rotating shaft 3, the other end of the binding belt 4 is fixed on the second end part 2; the second end part 2 is configured to be capable of being snap-fitted with the first end part 1; and the rotation-stopping structure 5 is provided between the first end part 1 and the rotating shaft 3, and the rotation-stopping structure 5 is configured to be capable of locking the rotating shaft 3 to the first end part 1.

In use, positions of a patient's autologous blood vessel that need to be anastomosed with two ends of an artificial blood vessel are taken as two broken ends of the patient's autologous blood vessel, a fixing ring is placed inside either broken end of the patient's autologous blood vessel, the artificial blood vessel is placed in a position to be anastomosed, and either end of the artificial blood vessel is inserted between an inner side of either end of the patient's autologous blood vessel and the fixing ring, respectively, then, the suture-free clasp for vascular anastomosis is snap-fitted outside the two broken ends of the patient's autologous blood vessel, wherein a snap-fitting process is as follows.

First, the second end part 2 and the first end part 1 are snap-fitted to each other; then, the rotating shaft 3 is rotated, so that the binding belt 4 is tightened until the artificial blood vessel is fixed to the two broken ends of the patient's autologous blood vessel, and the rotation-stopping structure 5 locks the rotating shaft 3 to the first end part 1, thus completing a knotting process; when it is necessary to readjust the knotting condition, the suture-free clasp for vascular anastomosis may be taken out just by releasing the snap-fit between the second end part 2 and the first end part 1, so as to knot again; alternatively, the locking state of the rotation-stopping structure 5 to the rotating shaft 3 is released, so that the binding belt 4 can be loosened or tightened again, so as to adjust the knotting strength and to knot again.

In the present embodiment, the vascular anastomosis operation is performed in a manner of rotating the rotating shaft 3 after snap-fitting the second end part 2 and the first end part 1 to each other so as to tighten the binding belt 4, in place of a manner of completely relying on the doctor to manually wind a silk thread or a silk belt, followed by binding in the prior art. In an operation process, as it is not required that the doctor's visual field and operation direction must be perpendicular to an axis of the blood vessel, the influence of the doctor's human factors on the knotting position in the vascular anastomosis is reduced; meanwhile, the manner of rotating the rotating shaft 3 to tighten the binding belt 4 can maintain the doctor's knotting strength within a certain range of stable force, further avoiding occurrence of the situation in which the knotting force is too low to cause slippage of the knot or the knotting force is too large to cause a cutting effect on the patient's autologous blood vessel and other situations; moreover, the operation thereof is simpler and more convenient compared with the prior art, and when it is necessary to readjust the knocking condition, the suture-free clasp for vascular anastomosis may be taken out just by releasing the snap-fit between the second end part 2 and the first end part 1 so as to knot again, alternatively, the binding belt 4 can be loosened or tightened again just by releasing the locking state of the rotation-stopping structure 5 to the rotating shaft 3, so as to adjust the knotting strength and to knot again, which is convenient for the doctor to adjust the knocking situation.

To sum up, the present embodiment at least has the above beneficial effects of reducing the influence of human factors of doctors on the knotting position and knotting strength in the vascular anastomosis, further solving the technical problems of difficult knotting operation, easy slippage of the knot to cause blood leakage and thereby form pseudoaneurysm, and difficult readjustment after the knotting is completed, existing in the prior art.

Further, in the present embodiment, the rotation-stopping structure 5 is of varied structures, for example, the rotation-stopping structure includes an opening provided on the first end part 1 and the rotating shaft 3, respectively, and a fixing pin capable of passing through the first end part 1 and the rotating shaft 3 in sequence, and the first end part 1 and the rotating shaft 3 are fixed by the fixing pin. Preferably, referring to FIG. 1, in combination with FIG. 2 to FIG. 5, in an optional embodiment of the present example, the above rotation-stopping structure 5 includes a ratchet 51 and a pawl 52; the ratchet 51 is formed on a circumferential surface of the rotating shaft 3; one end of the pawl 52 is connected to the first end part 1, and the pawl 52 is configured to always have a moving tendency to slide towards a position between roots of two adjacent teeth of the ratchet 51, so that in the whole knotting process, the pawl 52 may be configured to cooperate with the ratchet 51 at any time so as to lock or unlock the rotating shaft 3, which facilitates pausing or restarting the knotting process at any time when needed, improves the operability of the knotting process, and reduces the operation difficulty.

Figure 3:
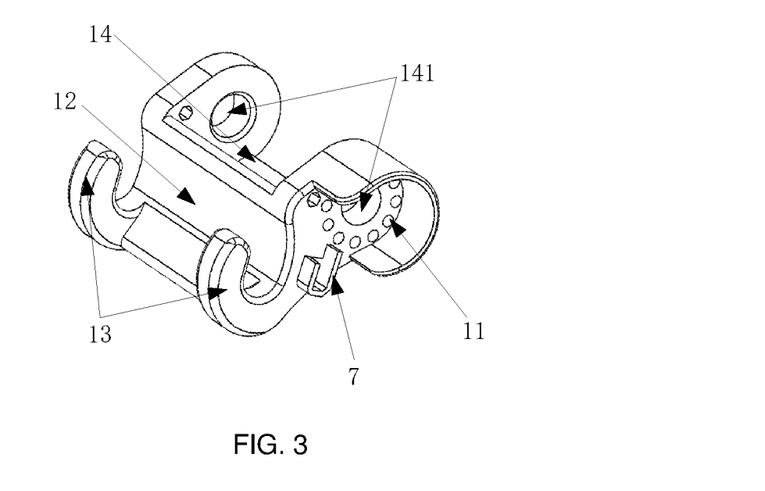
FIG. 3 is a schematic view of a whole structure of a first end part in the suture-free clasp for vascular anastomosis provided in an embodiment of the present disclosure.

In the above, the design of the pawl 52 may provide sufficient knotting strength, thus effectively preventing the rotating shaft 3 from rotating reversely, and the pawl 52 is connected to the first end part 1 in a variety of structure forms, for example, without limitation, one end of the pawl 52 being fixedly connected to the first end part 1. Preferably, in the above optional embodiment, further optionally, one end of the pawl 52 is detachably connected to the first end part 1, specifically, as shown in FIG. 3, the first end part 1 includes a first end part body and a limiting portion 7 provided on the first end part body, the limiting portion 7 and the first end part body may be integrally formed, as an integral structure, or also may be a structure fixed on the first end part body, the limiting portion 7 has an accommodating groove, a fitting hole is provided on the first end part body in a position corresponding to the accommodating groove of the limiting portion 7, a fitting portion is connected to one end of the pawl 52, and the fitting portion is fitted into the fitting hole of the first end part body, and an end portion of an end of the pawl 52 connected to the fitting portion is clamped in the accommodating groove of the limiting portion 7. Certainly, a specific connection manner in which one end of the pawl 52 is detachably connected to the first end part 1 may also be other detachable connection forms, for example, the limiting portion 7 described above is not provided, the fitting hole is only provided on the first end part 1, one end of the pawl 52 is connected with the fitting portion, the fitting portion is fitted into the fitting hole in the first end part 1, and the fitting portion is in interference fit with a hole wall of the fitting hole.

In a preferred optional embodiment, one end of the pawl 52 is connected to the first end part 1 in a detachable manner, thus, when the knotting condition needs to be readjusted, in addition to taking out the suture-free clasp for vascular anastomosis by releasing the snap-fit between the second end part 2 and the first end part 1 so as to knot again, the binding belt 4 may also be released by removing the pawl 52, then the binding belt 4 is retightened after the pawl 52 is reinstalled, so as to realize the function of adjusting the knotting strength.

In addition, on the basis of the above optional embodiment, further optionally, the pawl 52 is made of an elastic material, thus, when the rotating shaft 3 is rotated forward, the pawl 52 may be matched with the rotation of the ratchet 51 by the elasticity of the pawl, so that in the process of rotating the rotating shaft 3 to tighten the binding belt 4, the forward rotation of the rotating shaft 3 can be simultaneously realized and the reverse rotation thereof can be prevented without removing the pawl 52, thus, the structure thereof is simple, and there are the beneficial effects of simplifying the parts, and avoiding the functional failure of the suture-free clasp for vascular anastomosis in the case of more parts, wherein the elastic material may be of a metal material or other materials having certain elasticity, which is not further limited herein.

Figure 6:
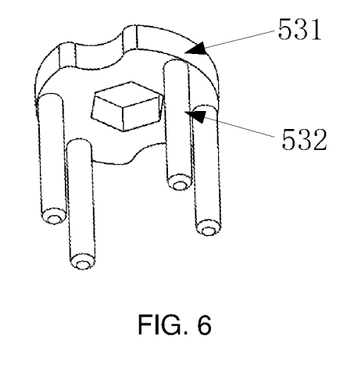
FIG. 6 is a schematic view of a whole structure of the end protective cover in the suture-free clasp for vascular anastomosis provided in an embodiment of the present disclosure.

In addition, referring to FIG. 1 and FIG. 6, on the basis of any of the above optional embodiments, further optionally, the rotation-stopping structure 5 includes the ratchet 51 and an end protective cover 53; the ratchet 51 is formed on the circumferential surface of the rotating shaft 3; the first end part 1 is provided with fixing holes 11 in positions between adjacent teeth of the ratchet 51; the end protective cover 53 includes a cover body 531 and pins 532 connected to the cover body 531; the fixing holes 11 and the pins 532 are respectively at least two, preferably, four or more; at least two pins 532 are correspondingly inserted into the fixing holes 11, thus the rotating shaft 3 may be further positioned and protected by the end protective cover 53, thereby avoiding the rotation of the rotating shaft 3 relative to the first end part 1, so as to ensure that the binding belt 4 has a good binding effect on the artificial blood vessel. The protective cover 53 can prevent the rotating shaft 3 from rotating reversely and also can prevent the rotating shaft from rotating forward, so as to be suitable for being provided in a preset position after the knotting process is completed, to further position the rotating shaft 3, moreover, the protective cover 53 can cover the outside of the ratchet 51, so that an operator cannot directly contact the ratchet 51, thereby avoiding misoperation on the ratchet.

Figure 4:
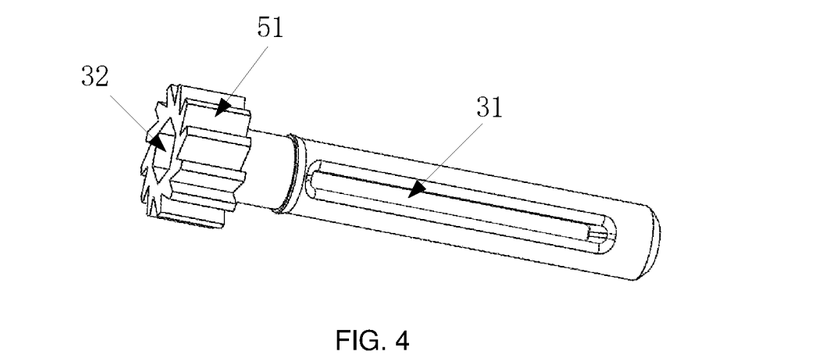
FIG. 4 is a schematic view of a whole structure of a rotating shaft in the suture-free clasp for vascular anastomosis provided in an embodiment of the present disclosure.
Figure 5:
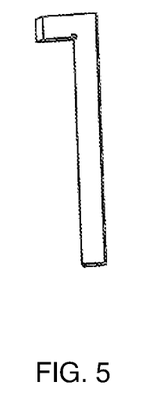
FIG. 5 is a schematic view of a whole structure of a pawl in the suture-free clasp for vascular anastomosis provided in an embodiment of the present disclosure.

In addition, referring to FIG. 4, in an optional embodiment of the present example, a long hole 31 is provided in the middle of the rotating shaft 3, and the binding belt 4 is fixed on the rotating shaft 3 in a manner that one end of the binding belt is threaded through the long hole 31 and then is joined with a remaining part of the binding belt 4, wherein a joining manner is, for example, but not limited to, gluing, welding, heat sealing or stitching. Certainly, in other optional embodiments of the present example, the binding belt 4 may also be directly glued on the rotating shaft 3, however, obviously, in contrast, by fixing one end of the binding belt 4 on the rotating shaft 3 according to the structure in FIG. 4, the fixing structure thereof is more stable, which is beneficial to avoiding slippage of the binding belt 4 from the rotating shaft 3, and meanwhile avoiding slipping of the binding belt 4 in the rotating process of the rotating shaft 3, so as to improve the success rate of operation and the durability of operation effect.

In addition, referring to FIG. 1 and FIG. 3, in an optional embodiment of the present example, the second end part 2 includes a rod portion 21 and end flanges 22 respectively formed at both ends of the rod portion 21, and the end flanges 22 may be an integral structure integrally formed with the rod portion 21, or may be a structure fixed on the rod portion 21; the first end part 1 is provided with a snap-fit groove 12 and an arc-shaped fixing portion 13; the snap-fit groove 12 is configured to be capable of accommodating the rod portion 21; and the arc-shaped fixing portion 13 is formed at either end of the snap-fit groove 12 in a length direction, and is configured to be capable of being clamped with the end flange 22. With such a structure, it is advantageous for the second end part 2 to be stably buckled on the first end part 1, thus sufficiently avoiding occurrence of loosening phenomenon.

Besides, in the present embodiment, the rotating shaft 3 is rotationally installed on the first end part 1 in a plurality of mounting manners, for example, referring to FIG. 1 and FIG. 3, in an optional embodiment of the present example, the first end part 1 is provided with a rotating shaft mounting groove 14, a mounting hole 141 is provided on an end surface of either end of the rotating shaft mounting groove 14, one end of the rotating shaft 3 is inserted into one of the mounting holes 141, and the other end of the rotating shaft 3 is inserted into the other mounting hole 141, so that the rotating shaft 3 is rotationally mounted on the first end part 1. Further, referring to FIG. 4, preferably, the rotating shaft 3, made of a polymer injection molding material, has certain elasticity, so that under the working condition that the rotating shaft 3 is assembled in the two mounting holes 141, a part of the rotating shaft 3 located between the two mounting holes 141 is an assembling part of the rotating shaft 3, and a cross-sectional area of the assembling part of the rotating shaft 3 is slightly larger than the aperture of the two mounting holes 141, thus, in the assembling process, the above assembling part of the rotating shaft 3 may be extruded through the two mounting holes 141 by means of an elastic force of the rotating shaft, and after passing, the assembling part of the rotating shaft 3 is just limited between the two mounting holes 141, thus, the rotating shaft 3 can be avoided from sliding out of the mounting holes 141, further ensuring that the rotating shaft 3 is stably connected in the two mounting holes 141.

In addition, in order to enable the suture-free clasp for vascular anastomosis to be well attached to a blood vessel wall of the artificial blood vessel so as to prevent blood leakage, in an optional embodiment of the present example, preferably, a side of the first end part 1 attached to the artificial blood vessel is in an arc shape.

In addition, referring to FIG. 2 and FIG. 4, in an optional embodiment of the present example, an operating portion 32 is provided at an end portion of the rotating shaft 3, and the operating portion 32 is configured to be capable of cooperating with a surgical instrument so as to rotate the rotating shaft 3. Specifically, as shown in FIG. 2 and FIG. 4, a polygonal operation hole is provided in the end portion of the rotating shaft 3 as the operating portion 32, thus, when the rotating shaft 3 is rotated, a dedicated surgical wrench can be extended into the operation hole to rotate the rotating shaft 3, which has the beneficial effects of a simple structure, a convenient operation, and a stable and reliable rotation process. Certainly, the operating portion 32 further may be formed in other structural forms, for example, the above operating portion 32 is a polygonal protrusion formed in the end portion of the rotating shaft 3, and the rotating shaft 3 is rotated by a dedicated surgical wrench sheathed outside the polygonal protrusion.

In particular, in the present optional embodiment, a rotation manner of rotating the rotating shaft 3 with the surgical instrument is provided. However, the present disclosure is not limited thereto, and it is also feasible that the above operating portion 32 is not provided, while the surgical operation is performed using a surgical instrument capable of directly clamping the end portion of the rotating shaft 3 and driving the rotating shaft 3 to rotate. However, in contrast, it is obvious that the process of rotating the rotating shaft 3 with the surgical instrument is more convenient and more reliable by providing the dedicated operating portion 32 above, which is beneficial to shorten the surgical time and ensure stable proceeding of the rotation process, accordingly, in various optional manners of rotating the rotating shaft 3 with the surgical instrument, preferably, the structure in the above optional embodiment is used, that is, providing the above operating portion 32.

Further, in an optional embodiment of the present example, a marker 6 is provided on at least one of a middle portion of the binding belt 4, the rotating shaft 3, and the second end part 2. Referring to FIG. 2, it shows that the marker 6 is provided on the middle portion of the binding belt 4. In the above, the above marker 6 is generally made of a metal, for example, but not limited to, noble metal materials such as gold wire or platinum iridium alloy wire, for developing and observing the position of the suture-free clasp for vascular anastomosis through X-ray irradiation in follow-up visit later, and confirming whether the suture-free clasp for vascular anastomosis is displaced or deformed, etc. There are a plurality of specific arrangement forms in which the marker 6 is provided on at least one of the middle portion of the binding belt 4, the rotating shaft 3, and the second end part 2, for example, the marker 6 is heat-sealed or injection-molded on a corresponding structural member, as long as it can be connected to a corresponding part.

In addition, in an optional embodiment of the present example, scales are set on an outer peripheral surface of the binding belt 4 after the binding belt is snap-fitted, wherein the scales may be in units such as centimeters, millimeters, and inches, so that when the second end part 2 is snap-fitted to the first end part 1, the medical personnel can clearly and visually know dimension information such as diameter and circumference of a closed loop formed by the binding belt 4, thus, it is convenient to adjust the knotting position and the knotting strength in practical operations according to the dimension of the blood vessel.

In addition, in an optional embodiment of the present example, the binding belt 4 is made of a flexible material, and has a certain frictional force with the vascular wall, which can avoid slippage of the knot to cause blood leakage and thereby form pseudoaneurysm.

Finally, it should be explained that the various examples above are merely used for illustrating the technical solutions of the present disclosure, rather than limiting the present disclosure; although the detailed description is made to the present disclosure with reference to various preceding embodiments, those ordinarily skilled in the art should understand that they still could modify the technical solutions recited in various preceding embodiments, or make equivalent substitutions to some or all of the technical features therein; and these modifications or substitutions do not make the corresponding technical solutions essentially depart from the scope of the technical solutions of various embodiments of the present disclosure.

INDUSTRIAL APPLICABILITY

The present disclosure provides a suture-free clasp for vascular anastomosis, which can reduce the influence of human factors of doctors on the knotting position and knotting strength in the vascular anastomosis, further solve the technical problems of difficult knotting operation, easy slippage of the knot to cause blood leakage and thereby form pseudoaneurysm, and difficult readjustment after the knotting is completed, existing in the prior art.

What is claimed is:

1. A suture-free clasp for vascular anastomosis, comprising a first end part, a second end part, a rotating shaft, a binding belt and a rotation-stopping structure, wherein
the rotating shaft is rotationally installed on the first end part; the binding belt has one end fixed on the rotating shaft, and the other end fixed on the second end part; and the second end part is configured to be capable of being snap-fitted with the first end part; and
the rotation-stopping structure is provided between the first end part and the rotating shaft, and the rotation-stopping structure is configured to be capable of locking the rotating shaft to the first end part,
wherein the rotation-stopping structure comprises a ratchet and an end protective cover, wherein
the ratchet is provided on a circumferential surface of the rotating shaft;
the first end part is provided with fixing holes in positions between adjacent teeth of the ratchet; and the end protective cover comprises a cover body and pins connected to the cover body; and
at least two fixing holes and at least two pins are provided, respectively; and the at least two pins are correspondingly inserted inside the fixing holes.

2. The suture-free clasp for vascular anastomosis according to claim 1, wherein the rotation-stopping structure further comprises and a pawl,
the pawl has one end connected to the first end part, and the pawl is configured to always have a moving tendency to slide towards a position between roots of two adjacent teeth of the ratchet.

3. The suture-free clasp for vascular anastomosis according to claim 2, wherein the one end of the pawl is connected to the first end part in a detachable manner.

4. The suture-free clasp for vascular anastomosis according to claim 2, wherein the first end part comprises a first end part body and a limiting portion provided on the first end part body.

5. The suture-free clasp for vascular anastomosis according to claim 4, wherein the limiting portion and the first end part body are integrally formed, as an integral structure.

6. The suture-free clasp for vascular anastomosis according to claim 4, wherein the limiting portion is a structure fixed on the first end part body.

7. The suture-free clasp for vascular anastomosis according to claim 4, wherein the limiting portion has an accommodating groove, and a fitting hole is provided, on the first end part body, in a position corresponding to the accommodating groove of the limiting portion.

8. The suture-free clasp for vascular anastomosis according to claim 7, wherein a fitting portion is connected to one end of the pawl, wherein the fitting portion is fitted into the fitting hole in the first end part body, and an end portion of an end of the pawl connected to the fitting portion is clamped in the accommodating groove of the limiting portion.

9. The suture-free clasp for vascular anastomosis according to claim 1, wherein a long hole is provided in a middle portion of the rotating shaft, and the binding belt is fixed on the rotating shaft in a manner that one end of the binding belt is threaded through the long hole and then is stitched with a remaining part of the binding belt.

10. The suture-free clasp for vascular anastomosis according to claim 1, wherein a long hole is provided in a middle portion of the rotating shaft, and the binding belt is fixed on the rotating shaft in a manner that one end of the binding belt is threaded through the long hole and then is joined with a remaining part of the binding belt.

11. The suture-free clasp for vascular anastomosis according to claim 10, wherein the binding belt is fixed on the rotating shaft in a manner that one end of the binding belt is threaded through the long hole and then is glued, welded, heat-sealed or stitched with a remaining part of the binding belt.

12. The suture-free clasp for vascular anastomosis according to claim 1, wherein the second end part comprises a rod portion and end flanges respectively provided at both ends of the rod portion; and the first end part is provided with a snap-fit groove and arc-shaped fixing portions, wherein the snap-fit groove is configured to be capable of accommodating the rod portion; and the arc-shaped fixing portions are provided at both ends of the snap-fit groove in a length direction, and is configured to be capable of being clamped with the end flanges.

13. The suture-free clasp for vascular anastomosis according to claim 1, wherein the first end part is provided with a rotating shaft mounting groove, mounting holes are provided on end surfaces of both ends of the rotating shaft mounting groove, the rotating shaft has one end inserted into one of the mounting holes, and the other end inserted into the other mounting hole.

14. The suture-free clasp for vascular anastomosis according to claim 1, wherein a side of the first end part attached to an artificial blood vessel is in an arc shape.

15. The suture-free clasp for vascular anastomosis according to claim 1, wherein a marker is provided on at least one of a middle portion of the binding belt, the rotating shaft, and the second end part.

16. The suture-free clasp for vascular anastomosis according to claim 1, wherein an operating portion is provided at an end portion of the rotating shaft, wherein the operating portion is configured to be capable of cooperating with a surgical instrument so as to rotate the rotating shaft.

17. The suture-free clasp for vascular anastomosis according to claim 16, wherein the operating portion is a polygonal operation hole provided in the end portion of the rotating shaft.

18. The suture-free clasp for vascular anastomosis according to claim 16, wherein the operating portion is a polygonal protrusion provided on the end portion of the rotating shaft.

* * * * *